(12) United States Patent
Chollet et al.

(10) Patent No.: US 8,455,487 B2
(45) Date of Patent: Jun. 4, 2013

(54) METHODS OF CONTROLLING INSECTS

(75) Inventors: Pascal Chollet, Nyon (CH); Domingos Pedroni, Basel (CH); Stephen Wilson Skillman, Basel (CH)

(73) Assignee: Syngenta Participations AG, Basel (CH)

( * ) Notice: Subject to any disclaimer, the term of this patent is extended or adjusted under 35 U.S.C. 154(b) by 572 days.

(21) Appl. No.: 12/601,596

(22) PCT Filed: May 20, 2008

(86) PCT No.: PCT/EP2008/004023
§ 371 (c)(1),
(2), (4) Date: May 11, 2010

(87) PCT Pub. No.: WO2008/151708
PCT Pub. Date: Dec. 18, 2008

(65) Prior Publication Data
US 2010/0222351 A1     Sep. 2, 2010

(30) Foreign Application Priority Data

Jun. 15, 2007  (EP) .................................... 07011725

(51) Int. Cl.
*A01N 43/707* (2006.01)
*A01N 25/12* (2006.01)
*A01N 25/14* (2006.01)
*A01P 7/04* (2006.01)

(52) U.S. Cl.
USPC ........................... 514/242; 514/951; 514/952

(58) Field of Classification Search
USPC ............................ 514/252.03, 242
See application file for complete search history.

(56) References Cited

U.S. PATENT DOCUMENTS

2004/0078843 A1    4/2004  Kern

FOREIGN PATENT DOCUMENTS

| DE | 102004021566 | | 6/2005 |
|---|---|---|---|
| EP | 0314615 | | 5/1989 |
| GB | 2270469 | | 3/1994 |
| WO | 9847368 | | 10/1998 |
| WO | WO 99-35910 | * | 7/1999 |
| WO | 0068222 | | 11/2000 |

OTHER PUBLICATIONS

B. Sechser, B. Reber, F. Bourgeois: "Pymetrozine: Selectivity spectrum to beneficial arthropods and fitness for integrated pest management"; Journal of Pest Science, vol. 75, No. 3, Jun. 2002, pp. 72-77, XP002458382.

* cited by examiner

*Primary Examiner* — John Pak
(74) *Attorney, Agent, or Firm* — Brian McAlhaney

(57) ABSTRACT

The invention relates to a method of controlling insects in the family Nitidulidae using the compound 4,5-di-hydro-6-methyl-4-(3-pyridylmethyleneamino)-1,2,4-triazin-3(2H)-one and also encompasses the use of compositions comprising 4,5-dihydro-6-methyl-4-(3-pyridylmethyleneamino)-1,2,4-triazin-3(2H)-one for controlling Nitidulidae, in particular pollen beetles as well as the preparation of said compound and/or compositions for use in controlling Nitidulidae. In particular, the invention relates to the use of 4,5-dihydro-6-methyl-4-(3-pyridylmethyleneamino)-1,2,4-triazin-3(2H)-one and/or compositions comprising this compound in controlling such insects in crops of useful plants, in particular flowering crops and/or flowering ornamental plants.

11 Claims, No Drawings

METHODS OF CONTROLLING INSECTS

This application is a 371 of International Application No. PCT/EP2008/004023 filed May 20, 2008, which claims priority to EP 07011725.4 filed Jun. 15, 2007, the contents of which are incorporated herein by reference.

The invention relates to a method of controlling insects in the family Nitidulidae, using compounds of formula I

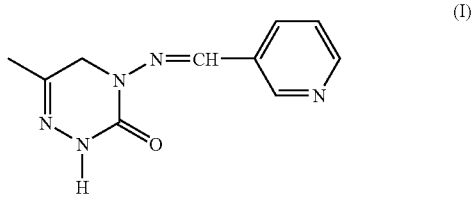 [SMILES: CC1=NNC(=O)N(N=Cc2cccnc2)C1]

(I)

in free form or in agrochemically acceptable salt form. The invention also encompasses the use of compositions comprising compounds of formula I for controlling Nitidulidae, in particular pollen beetles (insects of the genus *Meligethes*), as well as the preparation of such compounds and compositions for use in controlling Nitidulidae. In particular, the invention relates to the use of compounds of formula I and/or composition comprising compounds of formula I in controlling such insects in crops of useful plants, in particular flowering crops and/or flowering ornamental plants.

The compound of formula I (4,5-dihydro-6-methyl-4-(3-pyridylmethyleneamino)-1,2,4-triazin-3(2H)-one; pymetrozine) is known and described, for example, in EP 0314615. EP 0314615 gives a general description of the activity of compounds of the formula (II)

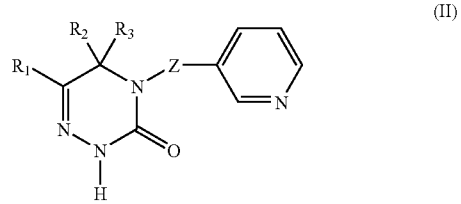

(II)

in free form or in acid addition salt form, wherein either $R_1$ is hydrogen, $C_1$-$C_{12}$ alkyl, $C_3$-$C_6$ cycloalkyl, $C_1$-$C_4$ alkoxy-$C_1$-$C_6$ alkyl, halo-$C_1$-$C_2$ alkyl, phenyl, benzyl, phenethyl, phenylpropyl, phenylbutyl or phenylpentyl, or a phenyl, benzyl, phenethyl, phenylpropyl, phenylbutyl or phenylpentyl radical mono- or all-substituted by halogen, $C_1$-$C_5$ alkyl, halo-$C_1$-$C_2$ alkyl, methoxy and/or by ethoxy, and $R_2$ is hydrogen, $C_1$-$C_6$ alkyl or $C_3$-$C_6$ cycloalkyl, or phenyl that is unsubstituted or substituted by $C_1$-$C_{12}$ alkyl, halogen or by halo-$C_1$-$C_{12}$ alkyl; or $R_1$ and $R_2$ together form a saturated or unsaturated 3- to 7-membered carbocycle; $R_3$ is hydrogen or $C_1$-$C_6$ alkyl; and Z is —N═CH—, or —NH—CH$_2$—, in the control of pests, especially insects, more especially insects of the orders Anoplura, Coleoptera, Diptera, Heteroptera, Hemiptera, Hymenoptera, Isoptera, Lepidoptera, Mallophaga, Orthoptera, Psocoptera, Siphonaptera, Thysanoptera and Thysanura, especially sucking insects of the Aphididae family, which belongs to the order Hemiptera. Despite this apparently broad disclosure of the utility of compounds of formula II, EP-A-0 314 615 specifically demonstrates the activity of compounds of formula II against only three insect species from the order Hemiptera, (namely the species *Aphis craccivora*, *Aphis fabae* and *Myzus persicae*) and only one species from the order Diptera (namely the species *Aedes aegypti*): no insects from orders other than Hemiptera and Diptera are shown to be target insects.

Subsequent literature reveals that 4,5-dihydro-6-methyl-4-(3-pyridylmethyleneamino)-1,2,4-triazin-3(2H)-one (pymetrozine) is inactive against several families of insect in the order Coleoptera (see, for example, Sechser et al. 2002 J. Pest Science 75:72-77 where pymetrozine is shown to have no effect on insects from the Coccinellidae, Carabidae and Staphylinidae families).

In view of the above findings by Sechser et al. it is highly surprising that it has now been found that 4,5-dihydro-6-methyl-4-(3-pyridylmethyleneamino)-1,2,4-triazin-3(2H)-one is particularly efficacious at controlling other insects in the order Coleoptera, namely insects from the family Nitidulidae.

Insects of the Nitidulidae are commonly known as sap-feeding beetles. Several members of this family, in particular members of the genus *Meligethes* (pollen beetles), are known to be important agronomic pests in a variety of commercially important flowering crops and flowering ornamental plants. For example, pollen beetles are known to attack crops in the following families: Brassicaceae (mustard family), Fabaceae (pea family), Labiatae (mint family; also known as Lamiaceae), Rosaceae (rose family) and Amaryllidaceae (amaryllis family). In particular, pollen beetle is a serious threat to crops of oilseed rape (canola), see for example, Boudreault et al. 2003 (Canadian Entomoligist 135(3):405-413) and mustard, as well as turnip and swede. Typically pollen beetle has been controlled through the use of pyrethroid insecticides, however, in recent years widespread resistance to this type of insecticide has emerged and this poses a serious problem to the growth of such a commercially important crop, in particular where no other insecticide have been approved for use in controlling this pest (Hansen, 2003, Pest Management Science 59:1057-1059).

With the emergence of resistance to pyrethroid insecticides there exists a need to find alternative methods of controlling insects of the Nitidulidae family, in particular those of the genus *Meligethes*, in crops of useful plants. The present invention makes use of the unexpected finding that 4,5-dihydro-6-methyl-4-(3-pyridylmethyleneamino)-1,2,4-triazin-3 (2H)-one is effective at controlling such insects and thus addresses this problem and also provides an alternative method of controlling Nitidulidae.

Thus in a first aspect the present invention provides a method of controlling insects, which comprises applying the active ingredient 4,5-dihydro-6-methyl-4-(3-pyridylmethylene-amino)-1,2,4-triazin-3(2H)-one in free form or in agrochemically acceptable salt form to insects of the family Nitidulidae.

By the terms "control" or "controlling" it is meant that, insects are repelled, are unable to feed and/or are killed, thus the method of the invention may involve the use of an amount of the active ingredient that is sufficient to repel insects (i.e a repellently effective amount of active ingredient), an amount of the active ingredient that is sufficient to stop insects feeding, or it may involve the use of an insecticidally effective amount of active ingredient (i.e. an amount sufficient to kill insects), or any combination of the above effects.

By virtue of the surprising ability of 4,5-dihydro-6-methyl-4-(3-pyridylmethylene-amino)-1,2,4-triazin-3(2H)-one to control insects of the Nitidulidae family, the invention also provides a method of protecting a crop of useful plants, wherein said crop is susceptible to and/or under attack from such insects. Such a method involves applying 4,5-dihydro- 6-methyl-4-(3-pyridylmethyleneamino)-1,2,4-triazin-3 (2H)-one in free form or in agrochemically acceptable salt form to said crop and/or said insects.

Crops of useful plants that may be protected according to this aspect of the invention include flowering crop plants and/or flowering ornamental plants. Flowering crop plants include for example, members of the Brassicacae, Labiatae and Fabaceae families, and flowering ornamental plants include in particular members of the Labiatae, Fabaceae, Rosaceae and Amaryllidaceae families. In preferred embodiments, flowering crops of oilseed rape (spring and/or winter varieties), mustard, turnip, swede, runner beans and lavender are protected by the application of 4,5-dihydro-6-methyl-4-(3-pyridylmethyleneamino)-1,2,4-triazin-3(2H)-one to the crop and/or insect pest. In further preferred embodiments the following ornamental plants may be protected against attack/infestation from insects of the Nitidulidae family: roses, lavender, daffodils, and sweet pea.

Crops of useful plants are to be understood as including those which are/have been made tolerant to herbicides or classes of herbicide and/or insecticide or classes of insecticide, and/or which have acquired a so-called "output" trait (e.g. improved storage staibilty, higher nutritional value, improved yield etc.) by conventional plant-breeding or genetic engineering methods. Examples of useful plants that have been rendered tolerant to herbicides by genetic engineering methods include e.g. glyphosate- and glufosinate-resistant varieties available under the trade names RoundupReady® and LibertyLink®, (e.g. RoundupReady® Canola and LibertyLink® Canola). An example of a crop that has been rendered tolerant to imidazolininone herbicides (e.g. imazamox) by conventional breeding methods includes Clearfield® summer rape (canola).

Thus useful plants include those where the plants are transgenic, or where the plants have inherited a trait as a consequence of the introduction at least one transgene in their lineage.

As shown herein, the compound of formula I is surprisingly effective at controlling insects in the Nitidulidae family. The control of such insects is particularly important where it has been found that such insects exhibit resistance (or tolerance) to the insecticides that have hitherto been used for their control. Thus the methods of the invention not only have applicability against Nitidulidae that are sensitive to insecticides other than the compound of formula I, but also against Nitidulidae that are resistant to such other insecticides, in particular Nitidulidae resistant to pyrethroid and/or organophosphate resistant Nitidulidae.

In preferred embodiments of the aspects of the invention discussed herein, 4,5-dihydro-6-methyl-4-(3-pyridylmethyleneamino)-1,2,4-triazin-3(2H)-one is used to control insects of the genus *Meligethes*, commonly known as pollen beetles. Pollen beetles damage plants by attacking flower bunches as they form, and will attack individual flower buds and flowers. In the absence of control of pollen beetle, or where the level of control is poor, this can result in many flowers being destroyed. Where this occurs in crops of flowering plants, the knock-on effects are reduction in pollination, reduction in the amount of seed produced, and thus an adverse effect on the yield in crops infested with pollen beetle (Cook et al. 1999 "Pollen beetle, *Meligethes aeneus fabricius*, incidence in the composite hybrid winter oilseed rape, synergy" in Proceedings of the 10*th* International Rapeseed Congress, Canberra, Australia, 1999). Where this occurs in ornamental plants, in particular those grown for their flowers, it can be seen that the flower yield will be devastated. Thus, in further aspects the invention provides methods of increasing the yield from crops of useful plants that are under attack by insects from the genus *Meligethes* and/or maintaining yield or reducing yield loss from crops of useful plants that susceptible to attack by insects of the genus *Meligethes*.

As mentioned above, pollen beetle infestation has an adverse effect on the pollination of flowers (Cook at al. infra) thus in still further aspects the invention provides methods of increasing pollination in crops of useful plants that are under attack by insects from the genus *Meligethes* and/or maintaining pollination in crops of useful plants that susceptible to attack by insects of the genus *Meligethes*.

Pollen beetles have been shown to preferentially attack yellow-coloured flowers (Giamoustaris & Mithen 1996, Entomologia Experientalis et Applicata 80: 206-208), thus in certain embodiments (according to any aspect of the invention mentioned hereinbefore) 4,5-dihydro-6-methyl-4-(3-pyridylmethyleneamino)-1,2,4-triazin-3(2H)-one is used for insect control in crops of useful plants wherein said plants have yellow flowers.

The methods of the present invention may be used to control all insects of the genus *Meligethes*, of which, according to the Royal Horticultural Society, there are at least 35 different species in Great Britain. In particular, methods of the invention may be used in the control of the following species: *M. aeneus, M. viridescens, M. coeruleovirens* ,Forest., *M. viduatus* Sturm., *M. atratus* OI., *M. bidens* Bris., *M. maurus* Sturm., *M. lambaris* Sturm., *M. coracinus* Sturm., *M. picipes* Sturm., *M. rutundicallis* Bris., and *M. fulvipes* Bris (all of which are known to attack the Brassicaceae). In preferred embodiments the methods of the invention will be used to control *M. aeneus* and/or *M. viridescens*. *M. subfumatus* Gangl, which has been shown to attack Lavender, may also be controlled using methods of the invention.

The compound 4,5-dihydro-6-methyl-4-(3-pyridylmethyleneamino)-1,2,4-triazin-3(2H)-one and its agrochemically acceptable salts may be made, for example, as described in EP 0314615. Alternatively, it may be obtained commercially as a formulated composition, for example under the trade marks FULFILL®, CHESS®, and PLENUM®.

Agrochemically acceptable salts of the compounds of formula I are, for example, acid addition salts. Those salts are formed, for example, with strong inorganic acids, such as mineral acids, for example perchioric acid, sulfuric acid, nitric acid, nitrous acid, a phosphoric acid or a hydrohalic acid, with strong organic carboxylic acids, such as unsubstituted or substituted, for example halogen-substituted, $C_1$-$C_4$ alkanecarboxylic acids, for example formic acid, acetic acid or trifluoroacetic acid, unsaturated or saturated dicarboxylic acids, for example oxalic, malonic, succinic, maleic, fumaric or phthalic acid, hydroxycarboxylic acids, for example ascorbic, lactic, malic, tartaric or citric acid, or benzoic acid, or with organic sulfonic acids, such as unsubstituted or substituted, for example halogen-substituted, $C_1$-$C_4$ alkane- or arylsulfonic acids, for example methane- or p-toluene-sulfonic acid. In view of the close relationship between the compounds of formula I in free form and in the form of their agrochemically acceptable salts, hereinbefore and hereinafter any reference to the free compounds of formula I or their agrochemically acceptable salts is to be understood as including also the corresponding agrochemically acceptable salts or the free compounds of formula I, respectively, where appropriate and expedient. In preferred embodiments the methods of the invention employ the free form of 4,5-dihydro-6-methyl-4-(3-pyridylmethylene amino)-1,2,4-triazin-3(2H)-one.

The compound of formula I, in free form or in agrochemically acceptable salt form, are in the form of (E) or (Z) isomers, depending on whether the (—N═C(H)—) partial structure, which links the two heterocycles shown in the structural formula disclosed above, has the (E) or the (Z) configuration. Accordingly, hereinbefore and hereinafter the compounds I, in free form or in agrochemically acceptable salt form, are to be understood as being the corresponding (E) or (Z) isomers, in each case in pure form or in the form of (E)/(Z) mixtures, even if not specifically mentioned in every case. Preferably the compounds of formula I are in the (E) form.

The compound of formula I in free form or in agrochemically acceptable salt form, may be in the form of tautomers. For example, compound I which, according to the structural formula disclosed above, has a [—N=(H)—C(=O)—] partial structure may be in equilibrium with the tautomer that has a [—N=C(OH)—] partial structure instead of the [—N(H)—C(=O)—] partial structure. Accordingly, hereinbefore and hereinafter any reference to the compound of formula I in free form or in agrochemically acceptable salt form, is also, where appropriate, to be understood as including corresponding tautomers, even when the latter are not specifically mentioned in every case.

The compound of formula I (as well as all isomers and/or tautomers thereof) in free form, may also be in the form of any one of the solvates or hydrates as described in International Patent Publication Number WO 00/68222. In particular the dihydrate form of 4,5-dihydro-6-methyl-4-(3-pyridylmethyleneamino)-1,2,4-triazin-3(2H)-one is preferred for use in the invention.

In order to apply an active ingredient to insects of the Nitidulidae family and/or crops of useful plants as required by the methods of the invention said active ingredient may be used in pure form or, more typically, formulated into a composition which includes, in addition to said active ingredient, a suitable inert diluent or carrier and optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). SFAs include non-ionic, cationic and/or anionic surfactants, as well as surfactant mixtures.

Thus in further embodiments according to any aspect of the invention mentioned hereinbefore, the active ingredient will be in the form of a composition additionally comprising a agriculturally acceptable carrier or diluent.

It is preferred that all compositions (both solid and liquid formulations) for use in the invention comprise, by weight, from 0.0001 to 95% (inclusive), more preferably from 1 to 85% (inclusive), for example from 5 to 60% (inclusive), of active ingredient. The composition is generally used in methods of the invention such that the active ingredient is applied at a concentration are from 0.1 to 1000 ppm, preferably from 0.1 to 500 ppm, of active ingredient. In particular, spray mixtures with active ingredient concentrations of 50, 100, 200, 300 or 500 ppm are used. The rates of application per hectare are generally from 1 to 2000 g of active ingredient per hectare, especially from 10 to 1000 g/ha, preferably from 20 to 600 g/ha, more preferably from 12.5 to 300 g/ha. Rates of application of 50, 100, 150, 200, 250, 300, or 400 g of active ingredient per hectare are preferred.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing the active ingredient with one or more solid diluents (for example natural clays, kaolin, pyrophyllite, bentonite, alumina, montmorillonite, kieselguhr, chalk, diatomaceous earths, calcium phosphates, calcium and magnesium carbonates, sulfur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium bicarbonate, sodium carbonate or magnesium sulfate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing the active ingredient with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of the active ingredient and one or more powdered solid diluents or carriers, or from pre-formed blank granules by absorbing the active ingredient (or a solution thereof, in a suitable agent) in a porous granular material (such as pumice, attapulgite clays, fuller's earth, kieselguhr, diatomaceous earths or ground corn cobs) or by adsorbing the active ingredient (or a solution thereof, in a suitable agent) on to a hard core material (such as sands, silicates, mineral carbonates, sulfates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving the active ingredient in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving the active ingredient in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent) and then emulsifiying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. The active ingredient is present initially in either the water or the solvent/SFA blend. Suitable solvents for use in MEs include those hereinbefore described for use in ECs or in EWs. A ME may be either an oil-in-water or a water-in-oil system (which system is present may be determined by conductivity measurements) and may be suitable for mixing water-soluble and oil-soluble pesticides in the same formulation. A ME is suitable for dilution into water, either remaining as a microemulsion or forming a conventional oil-in-water emulsion.

Suspension concentrates (SC) may comprise aqueous or non-aqueous suspensions of finely divided insoluble solid particles the active ingredient. SCs may be prepared by ball or bead milling the solid active ingredient in a suitable medium, optionally with one or more dispersing agents, to produce a fine particle suspension of the compound. One or more wetting agents may be included in the composition and a suspending agent may be included to reduce the rate at which the particles settle. Alternatively, the active ingredient may be dry milled and added to water, containing agents hereinbefore described, to produce the desired end product.

Aerosol formulations comprise the active ingredient and a suitable propellant (for example n-butane). Active ingredients may also be dissolved or dispersed in a suitable medium (for example water or a water miscible liquid, such as n-propanol) to provide compositions for use in non-pressurised, hand-actuated spray pumps.

The active ingredient may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains the active ingredient and, optionally, a carrier or diluent therefor. The polymeric shell may be produced by either an interfacial polycondensation reaction or by a coacervation procedure. The compositions may provide for controlled release of the compound of the active ingredient. Active ingredients may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of the active ingredient. Such additives include surface active agents, spray additives based on oils, for example certain mineral oils, natural plant oils (such as soy bean and rape seed oil) and/or modified plant oils (e.g. esterified plant oils), and blends of these with other bio-enhancing adjuvants (ingredients which may aid or modify the action of the active ingredient.

Preferred compositions for use in methods of the invention are composed in particular of the following constituents (throughout, percentages are by weight):

Emulsifiable Concentrates (EC):

active ingredient: 1 to 90%, preferably 5 to 20%

SFA: 1 to 30%, preferably 10 to 20% solvent: 5 to 98%, preferably 70 to 85%

Dusts (DP):

active ingredient: 0.1 to 10%, preferably 0.1 to 1% solid carrier/diluent: 99.9 to 90%, preferably 99.9 to 99%

Suspension Concentrates (SC):

active ingredient: 5 to 75%, preferably 10 to 50% water: 94 to 24%, preferably 88 to 30%

SFA: 1 to 40%, preferably 2 to 30%

Wettable Powders (WP):

active ingredient: 0.5 to 90%, preferably 1 to 80%, more preferably 20 to 30%

SFA: 0.5 to 20%, preferably 1 to 15% solid carrier: 5 to 99%, preferably 15 to 98%

Granules (GR, SG, WG):

active ingredient: 0.5 to 60%, preferably 5 to 60%, more preferably 50 to 60% solid carrier/diluent; 99.5 to 40%, preferably 95 to 40%, more preferably 50 to 40%

In preferred embodiments the composition will be a DP, GR, WG or WP formulation, more preferably it will be a WG or WP formulation (e.g. CHESS® WG, PLENUM® WG, FULFILL® WG).

Where the active ingredient described herein is employed in methods of protecting crops of useful plants, methods of enhancing/maintaining yield and/or methods of increasing/maintaining pollination in crops of useful plants, it is preferred that said active ingredient (or compositions containing such active ingredient) is applied to the crop of useful plants at the flower-bud stage. In particular for crops of useful plants wherein said plants have yellow flowers, (e.g. oilseed rape, mustard etc.) it is preferred that the application occurs at the green to yellow bud stage.

The compound 4,5-dihydro-6-methyl-4-(3-pyridylmethylene amino)-1,2,4-triazin-3(2H)-one is known to be insecticidally efficacious against insects other than those of the Nitidulidae family at rates of 150 to 300 g active ingredient per hecatare (g ai/ha). The present invention may additionally exploit the unexpected finding that 4,5-dihydro-6-methyl-4-(3-pyridylmethylene amino)-1,2,4-triazin-3(2H)-one is efficacious against Nitidulidae at lower application rates. Thus, the rate of application of active ingredient per hectare (g ai/ha) will typically be in the range of 12.5 g ai/ha to 300 g ai/ha, preferably in the range 12.5 g ai/ha to 150 g ai/ha. In certain embodiments the application rate will be 12.5 g ai/ha, 50 g ai/ha, 100 g ai/ha, 150 g ai/ha or 200 g ai/ha.

Various aspects and embodiments of the present invention will now be illustrated in more detail by way of example. It will be appreciated that modification of detail may be made with out departing from the scope of the invention.

For the avoidance of doubt, where a literary reference, patent application, or patent, is cited within the text of this application, the entire text of said citation is herein incorporated by reference.

EXAMPLES

Formulation Examples (Throughout, Percentages are by Weight)

| Example F1: Solutions | a) | b) | c) | d) |
|---|---|---|---|---|
| active ingredient | 80% | 10% | 5% | 95% |
| ethylene glycol monomethyl ether | 20% | — | — | — |
| polyethylene glycol (mol. wt 400) | — | 70% | — | — |
| N-methyl-2-pyrrolidone | — | 20% | — | — |
| epoxidised coconut oil | — | — | 1% | 5% |
| petroleum fraction (boiling range 160-190.degree.) | — | — | 94% | — |

These solutions are suitable for application in the form of micro-drops.

| Example F2: Granules | a) | b) | c) | d) |
|---|---|---|---|---|
| active ingredient | 5% | 10% | 8% | 21% |
| Kaolin | 94% | — | 79% | 54% |
| Highly dispersed silicic acid | 1% | — | 13% | 7% |
| Attapulgite | — | 90% | — | 18% |

The active ingredient is dissolved in dichloromethane, the solution is sprayed onto the carrier, and the solvent is subsequently evaporated off in vacuo.

| Example F3: Dusts | a) | b) |
|---|---|---|
| active ingredient | 2% | 5% |
| Highly dispersed silicic acid | 1% | 5% |
| Talcum | 97% | — |
| Kaolin | — | 90% |

Ready-for-use dusts are obtained by intimately mixing the carriers with the active ingredient.

| Example F4: Wettable powders | |
|---|---|
| active ingredient | 25% |
| Sodium sulphate | 5% |
| castor oil polyethylene glycol ether (36-37 mol of ethylene oxide) | 10% |
| silicone oil | 1% |
| Agridex | 2% |
| highly dispersed silicic acid | 10% |
| kaolin powder | 37% |
| sulfite spent lye powder | 5% |
| Ultravon W-300% (disodium salt of 1-benzyl-2 heptadecylbenzimidazole-X,X'-disulfonic acid) | 5% |

The active ingredient is mixed with the other formulation components and the mixture is ground in a suitable mill, affording wettable powders which can be diluted with water to give suspensions of the desired concentration.

| Example F5: Dusts | a) | b) |
|---|---|---|
| active ingredient | 5% | 8% |
| Talcum | 95% | — |
| Kaolin | — | 92% |

Ready-for-use dusts are obtained by mixing the active ingredient with the carrier and grinding the mixture in a suitable mill.

| Example F6: Extruder granules | |
|---|---|
| active ingredient | 10% |
| Sodium lignosulfonate | 2% |
| Carboxymethylcellulose | 1% |
| Kaolin | 87% |

The active ingredient is mixed and ground with the other formulation components, and the mixture is subsequently moistened with water. The moist mixture is extruded and granulated and then the granules are dried in a stream of air.

| Example F7: Coated granules | |
|---|---|
| active ingredient | 3% |
| Polyethylene glycol (mol. wt. 200) | 3% |
| Kaolin | 94% |

The finely ground active ingredient is uniformly applied, in a mixer, to the kaolin moistened with polyethylene glycol. Non-dusty coated granules are obtained in this manner.

| Example F8: Suspension concentrate | |
|---|---|
| active ingredient | 40% |
| Ethylene glycol | 10% |
| Nonylphenol polyethylene glycol Ether (15 mol of ethylene oxide) | 6% |
| Sodium lignosulfonate | 10% |
| Carboxymethylcellulose | 1% |
| Aqueous formaldehyde solution (37%) | 0.2% |
| Aqueous silicone oil emulsion (75%) | 0.8% |
| Water | 32% |

The finely ground active ingredient is intimately mixed with the other formulation components giving a suspension concentrate from which suspensions of any desired concentration can be obtained by dilution with water.

| Example F9: Emulsifiable concentrates | a) | b) | c) |
|---|---|---|---|
| active ingredient | 25% | 40% | 50% |
| Calcium dodecylbenzenesulfonate | 5% | 8% | 6% |
| Castor oil polyethylene glycol ether (36 mol of ethylene oxide) | 5% | — | — |
| Tristyrylphenol polyethylene glycol ether (30 mol of ethylene oxide) | — | 12% | 4% |
| Cyclohexanone | — | 15% | 20% |
| Xylene mixture | 65% | 25% | 20% |

Emulsions of any desired concentration can be produced from such concentrates by dilution with water.

| Example F10: Wettable powders | a) | b) | c) |
|---|---|---|---|
| active ingredient | 25% | 50% | 75% |
| Sodium lignosulfonate | 5% | 5% | — |
| Sodium laurylsulfate | 3% | — | 5% |
| Sodium diisobutylnapthalene-sulfonate | — | 6% | 10% |
| Octylphenol polyethylene glycol ether (7-8 mol of ethylene oxide) | — | 2% | — |
| Highly dispersed silicic acid | 5% | 10% | 10% |
| Kaolin | 62% | 27% | — |

The active ingredient is mixed with the other formulation components and the mixture is ground in a suitable mill, affording wettable powders which can be diluted with water to give suspensions of the desired concentration.

| Example F11: Emulsifiable concentrate | |
|---|---|
| active ingredient | 10% |
| Octylphenol polyethylene glycol ether (4-5 mol of ethylene oxide) | 3% |
| Calcium dodecylbenzenesulfonate | 3% |
| Castor oil polyglycol ether (36 mol of ethylene oxide) | 4% |
| Cyclohexanone | 30% |
| Xylene mixture | 50% |

Emulsions of any required concentration can be obtained from this concentrate by dilution with water.

Biological Examples

B.1 Control of Pollen Beetle by 4,5-dihydro-6-methyl-4-(3-pyridylmethyleneamino)-1,2,4-triazin-3(2H)-one in Oilseed Rape: Comparison to Lavender oil and Quassan 30

A randomized complete block field trial was carried out on winter oilseed rape, which had reached crop stage BBCH 55 (flower buds, open flowers, some small seed pods formed) and which was under attack by actively foraging pollen beetles (adult beetles: 1 beetle/flower cluster). The active ingredient pymetrozine ((E)-4,5-dihydro-6-methyl-4-(3-pyridylmethyleneamino)-1,2,4-triazin-3(2H)-one; formulated as Plenum 50% WG) was tested at rates of 50 and 150 g ai/ha and compared to the activity of Lavender oil (at rates of 1000 g ai/ha and 2500 g ai/ha) and Quassia amara extract (Quassan 30; applied at rates of 30, 90 and 270 g ai/ha). Foliar application of the compounds under test was effected using a conventional spray boom and a volume of 500 L/ha. The degree of pest control was assessed pre-spray, and compared to that observed 1, 3 and 5 days after application. The data obtained is shown below in Table 1.

TABLE 1

| Treatment | Percentage Control | | |
|---|---|---|---|
| AI (g ai/ha) | 1 DAA | 3 DAA | 5 DAA |
| None | 0 | 0 | 0 |
| Pymetrozine 50 | 90 | 98 | 99 |
| Pymetrozine 150 | 86 | 92 | 95 |
| Lavender Oil 1000 | 9 | 34 | 10 |
| Lavender Oil 2500 | 26 | 16 | 12 |
| Lavender Oil 1000 | 15 | 24 | 31 |
| Quassan 30 30 | −93 | 5 | −6 |
| Quassan 30 90 | 2 | 14 | 20 |
| Quassan 30 270 | −19 | 4 | 42 |

With the exception of pymetrozine, all treatments exhibited very poor levels of pest control. Surprisingly, pymetrozine exhibited excellent control even at 1 day after application.

B.2 Control of Pollen Beetle by 4,5-dihydro-6-methyl-4-(3-pyridylmethyleneamino)-1,2,4-triazin-3(2H)-one in Oilseed Rape: Comparison to Lambda Cyhalothrin An unreplicated field test was carried out on Winter oilseed rape, (crop stage BBCH 55) and which was under attack by actively foraging pollen beetles (adult beetles: 2.32 beetle/flower cluster). The active ingredient pymetrozine ((E)-4,5-dihydro-6-methyl-4-(3-pyridylmethyleneamino)-1,2,4-triazin-3(2H)-one; formulated as Chess 50% WG) was tested at rates of 12.5, 50 and 200 g ai/ha and compared to the activity of lambda-cyhalothrin (formulated as Karate Zeon 10CS) at 5 g ai/ha. Foliar application of the compounds under test was effected using a conventional spray boom. The degree of pest infestation was assessed pre-spray (average of 2.3 adult pollen beetles per flower cluster in the check plot) and compared to that observed 1 day after application. The data obtained was converted to percentage of efficacy and is shown below in Table 2.

TABLE 2

| Treatment (g ai/ha) | % Control 1DAA |
|---|---|
| None | 0 |
| Lambda-cyhalothrin (5) | 100 |
| Pymetrozine (200) | 100 |
| Pymetrozine (50) | 98 |
| Pymetrozine (12.5) | 90 |

Again, it can be seen that 4,5-dihydro-6-methyl-4-(3-pyridylmethyleneamino)-1,2,4-triazin-3(2H)-one effected excellent control of *Meligethes* at all rates.

B.3 Control of Pollen Beetle by 4,5-dihydro-6-methyl-4-(3-pyridylmethyleneamino)-1,2,4-triazin-3(2H)-one in Oilseed Rape: Comparison to Lambda Cyhalothrin and Thiacloprid A third field trial (randomized complete block) was carried out on oilseed rape, which had reached crop stage BBCH 55 (new growth with 30 to 60 cm height; flower buds, open flowers, some small seed pods formed) and which was under attack by actively foraging pollen beetles (adult beetles: 10 beetle/flower cluster). The active ingredient pymetrozine ((E)-4,5-dihydro-6-methyl-4-(3-pyridylmethyleneamino)-1,2,4-triazin-3(2H)-one; formulated as Plenum 50% WG) was tested at rates of 50, 100 and 150 g ai/ha and compared to the activity of lambda cyhalothrin (7.5 g ai/ha) and thiacloprid (72 g ai/ha). Foliar application of the compounds under test was effected using a conventional spray boom and a volume of 400 L/ha. The degree of pest control was assessed pre-spray, and compared to that observed 2 hours, 1, 3 and 5 days after application. The data obtained is shown below in Table 3.

TABLE 3

| Treatment | % Control | | | |
|---|---|---|---|---|
| (g ai/ha) | 2 hrs aa | 1 DAA | 3 DAA | 5 DAA |
| None | 10.2* | 15.8* | 14.6* | 15.7* |
| Pymetrozine (50) | 37.3 | 19 | 44 | 0 |
| Pymetrozine (100) | 39.9 | 61 | 77 | 0 |
| Pymetrozine (150) | 42.5 | 61 | 84 | 0 |
| Thiacloprid (72) | 39.9 | 67 | 92 | 0 |
| Lambda cyhalothrin (7.5) | 63.4 | 75 | 92 | 23 |

*figures given for the control treatment (no active ingredient) represent the number of pollen beetles observed per flower cluster, not percentage control.

Even despite the extremely high pest pressure in this trial, pymetrozine still demonstrate efficacy at controlling Meligethes early after application, and at levels comparable to those exhibited by thiacloprid and lambda cyhalothrin.

B.4 Control of pyrethroid resistant Pollen Beetle by 4,5-dihydro-6-methyl-4-(3-pyridylmethyleneamino)-1,2,4-triazin-3(2H)-one in Oilseed Rape: Comparison to Lambda Cyhalothrin and Thiacloprid A further field trial (randomized complete block, 30 racemes per plot) was carried out on oilseed rape, which had reached crop stage BBCH 57-59 (individual flower buds—secondary inflorescence—visible but still closed) and which was under attack by actively foraging pollen beetles (adult beetles: average of 30 adult beetles/plot). The active ingredient pymetrozine ((E)-4,5-dihydro-6-methyl-4-(3-pyridylmethylene-amino)-1,2,4-triazin-3(2H)-one; formulated as Plenum 50% WG) was tested at rates of 50, 100 and 150 g ai/ha and compared to the activity of lambda cyhalothrin (7.5 g ai/ha) and thiacloprid (72 g ai/ha). Foliar application of the compounds under test was effected using a conventional spray boom and a volume of 500 L/ha. The degree of pest control was assessed pre-spray, and compared to that observed 1 and 3 days after application. The data obtained is shown below in Table 4.

TABLE 4

| Treatment | % Control | |
|---|---|---|
| (g ai/ha) | 1 DAA | 3 DAA |
| None | 22.3* | 24.8* |
| Pymetrozine (50) | 60 | 96 |
| Pymetrozine (100) | 62 | 97 |
| Pymetrozine (150) | 78 | 96 |
| Thiacloprid (72) | 63 | 94 |
| Lambda cyhalothrin (7.5) | 73 | 60 |

*figures given for the control treatment (no active ingredient) represent the average number of pollen beetles observed per plot, not percentage control.

At 3DAA, pymetrozine demonstrated greater efficacy (>90% control) at controlling Meligethes than that exhibited by lambda cyhalothrin. The level of control achieved by pymetrozine was equivalent to that observed by thiacloprid. The low level of control achieved by the recommended field rate of lambda cyhalothrin is indicative that the pollen beetles under test are resistant to pyrethroid insecticides.

B.5 Control of Pyrethroid Resistant Pollen Beetle by 4,5-dihydro-6-methyl-4-(3-pyridylmethyleneamino)-1,2,4-triazin-3(2H)-one in Oilseed Rape: Comparison to Lambda Cyhalothrin and Thiacloprid Three further field trials (randomized complete block, 25 plants per plot) were carried out on oilseed rape, which had reached crop stage BBCH 57-63 and which was under attack by actively foraging pollen beetles (adult beetles: average of 27 adult beetles/plot). The active ingredient pymetrozine ((E)-4,5-dihydro-6-methyl-4-(3-pyridylmethylene-amino)-1,2,4-triazin-3(2H)-one; formulated as Plenum 50% WG) was tested at rates of 75, 100 and 150 g ai/ha and compared to the activity of lambda cyhalothrin (7.5 g ai/ha) and thiacloprid (72 g ai/ha). Foliar application of the compounds under test was effected using a conventional spray boom and a volume of 300 L/ha. The degree of pest control was assessed pre-spray, and compared to that observed 1, 4 and 7 days after application. The data obtained from the three trials is shown below in Table 5.

TABLE 5

| Treatment | Mean % Control | | |
|---|---|---|---|
| (g ai/ha) | 1 DAA | 4 DAA | 7 DAA |
| None | 0 | 0 | 0 |
| Pymetrozine (75) | 89.9 | 72.4 | 92.8 |
| Pymetrozine (100) | 87.2 | 72.9 | 92.8 |
| Pymetrozine (150) | 95.2 | 77.4 | 91.3 |
| Thiacloprid (72) | 74.7 | 92.5 | 78.3 |
| Lambda cyhalothrin (7.5) | 33.0 | 20.0 | 18.1 |

The invention claimed is:

1. A method of controlling insects, which comprises applying the active ingredient 4,5-dihydro-6-methyl-4-(3-pyridylmethyleneamino)-1,2,4-triazin-3(2H)-one in free form or in agrochemically acceptable salt form, to insects of the family Nitidulidae.

2. The method according to claim 1, wherein said insects are of the species *Meligethes*.

3. The method according to claim 1, wherein said insects are selected from the group consisting of *Meligethes aeneus, Meligethes viridescens, Meligethes coracinus, Meligethes gracilis* and *Meligethes* sp. TJH-2004, *Meligethes coeruleovirens* Forest, *Meligethes viduatus* Sturm, *Meligethes atratus* Ol., *Meligethes bidens* Bris, *Meligethes maurus* Sturm., *Meligethes lambaris* Sturm., *Meligethes coracinus* Sturm, *Meligethes picipes* Sturm, *Meligethes rutundicallis* Bris and *Meligethes fulvipes* Bris.

4. The method according to claim 1, wherein said insects are resistant to pyrethroid insecticides.

5. The method according to claim 1, wherein the active ingredient is 4,5-dihydro-6-methyl-4-(3-pyridylmethyleneamino)-1,2,4-triazin-3(2H)-one dihydrate.

6. The method according to claim 1, wherein the active ingredient is in the form of a composition, said composition additionally comprising an agriculturally acceptable diluent or carrier.

7. The method according to claim 1, wherein said active ingredient is formulated as a water dispersible granule.

8. A method of protecting a crop of useful plants under attack by insects of the family Nitidulidae, which comprises applying to said crop and said insects the active ingredient 4,5-dihydro-6-methyl-4-(3-pyridylmethyleneamino)-1,2,4-triazin-3(2H)-one in free form or in agrochemically acceptable salt form.

9. The method according to claim 8, wherein said useful plants comprise flowering crop plants or flowering ornamental plants.

10. The method according to claim 9, wherein said flowering crop plants are oil seed rape plants.

11. The method according to claim 8, wherein said useful plants are transgenic plants.

* * * * *